United States Patent [19]

Dickneite et al.

[11] Patent Number: 4,847,299
[45] Date of Patent: Jul. 11, 1989

[54] USE OF 15-DEOXYSPERGUALINE AS A PHARMACEUTICAL

[75] Inventors: Gerhard Dickneite; Hans-Ulrich Schorlemmer; Hans P. Kraemer; Hans H. Sedlacek, all of Marburg, Fed. Rep. of Germany

[73] Assignee: Behringwerke Aktiengesellschaft, Marburg/Lahn, Fed. Rep. of Germany

[21] Appl. No.: 80,056

[22] Filed: Jul. 31, 1987

[30] Foreign Application Priority Data

Aug. 2, 1986 [DE] Fed. Rep. of Germany ....... 3626306

[51] Int. Cl.$^4$ .................... A61K 31/13; A61K 31/16
[52] U.S. Cl. .................................................. 514/579
[58] Field of Search ......................................... 514/579

Primary Examiner—Stanley J. Friedman
Attorney, Agent, or Firm—Finnegan, Henderson, Farabow, Garrett, & Dunner

[57] ABSTRACT

The use of 15-deoxyspergualine for the preparation of a pharmaceutical for the therapy of degenerative diseases is claimed.

8 Claims, No Drawings

USE OF 15-DEOXYSPERGUALINE AS A PHARMACEUTICAL

The invention relates to the use of 15-deoxyspergualine for the preparation of a pharmaceutical for humans and animals.

15-Deoxyspergualine was found by Prof. Umezawa and coworkers (European Pat. No. 83 104 712.1). Its antitumor activity and immunosuppressive properties have been described (European Pats. Nos. 83 104 712.1 and 85 114 042.6).

Surprisingly, it has now been found that, in addition to its immunosuppressive action, the substance has a dose-dependent stimulant effect on the colony-forming cells of the bone marrow, and thus has a therapeutic effect on various degenerative diseases even when its immunosuppressive action is negligible.

The degenerative diseases on which substances which have stimulant properties act on the bone marrow include bonemarrow diseases as well as degenerative diseases of the supporting and connective tissues (Gupta et al. Arthritis Rheum. 118, 179 (1975) and Amer. J. Med. 61, 29 (1976)).

It has now been found, in particular, that 15-deoxyspergualine has a therapeutic effect on degenerative disease of the central nervous system (CNS) using a dosage which has no immunosuppressive activity.

Accordingly, the invention relates to the use of 15-deoxyspergualine for the preparation of a pharmaceutical which stimulates the colony-forming cells of the bone marrow for the therapy of degenerative diseases. Diseases of this type are regarded as being, for example, bone-marrow diseases, diseases of the supporting and connective tissues, multiple sclerosis, nephritis and hepatitis.

Multiple sclerosis is a chronic degenerative disease of the central nervous system whose cause is substantially unknown. An experimental model for multiple sclerosis is regarded as being experimental allergic encephalomyelitis (EAE) induced in rats by administration of myelin, a substance from the central nervous system. The disease starts with paralysis of the extremities and finally results in the death of the animals. Administration of immunosuppressants in therapeutic tests of this type has hitherto shown only limited efficacy once the disease has become manifest. Surprisingly, 15-deoxyspergualine shows marked efficacy at suitable doses.

The compound can be used as a therapeutic agent for the treatment of degenerative diseases, bone-marrow diseases, diseases of the supporting and connective tissues, diseases of the central nervous system and, in particular, of multiple sclerosis, and kidney and liver diseases.

The effective lower limit of the dose of deoxyspergualine for this purpose is approximately in the region of 0.01 mg/kg of body weight on parenteral administration. It is limited by the toxicity of the substance, which is 13 mg/kg.

Thus the invention relates to a pharmaceutical containing 0.75 mg to 975 mg per dose (75 kg body weight) of 15-deoxyspergualine, preferably in the form of the more reasonably priced racemate, but in particular as (−)-15-deoxyspergualine. Suitable for oral or parenteral, specifically intravenous, administration are physiologically tolerated aqueous solutions or suspensions, which are known per se, of the active compound in a pharmaceutically tolerated vehicle, preferably vegetable oil, such as arachis oil or sesame oil, as well as alcoholic solutions of the active compound, for example in ethanol, propanediol or glycerol or in mixtures of the said solvents.

The effect of the substance in standard test methods is illustrated by way of example hereinafter.

EXAMPLE 1

Stimulation of colony-forming cells of the bone marrow by deoxyspergualine

Female B6D2FI mice were treated with the concentrations of 15-deoxyspergualine stated in Table 1. 15-Deoxyspergualine was administered intraperitoneally on 5 consecutive days. 7 days after the first treatment with 15-deoxyspergualine, the bone marrow was removed from the femurs of the sacrificed mice, and the selected cells with the ability to form colonies were determined. The method described by Stanley et al. (J. Exp. Med. 143, 631 (1976)), which is a soft agar technique, was used for this purpose. Table 1 shows dose-dependent stimulation of the colony-forming cells in the bone marrow of animals treated with 15-deoxyspergualine.

EXAMPLE 2

Therapeutic treatment of experimental allergic encephalomyelitis (EAE) with 15-deoxyspergualine EAE was induced in female Lewis rats by administration of guinea pig spinal cord, complete Freund's adjuvant and killed Bordetella pertussis germs. 15-Deoxyspergualine was administered either orally or intraperitoneally after induction, in a concentration of 0.16 to 2.5 mg/kg of body weight on five consecutive days.

Table 2 shows that the disease results in the death of all the animals in the untreated control group. The mean survival time was 15 to 16 days.

Administration of 15-deoxyspergualine results in a dose-dependent mortality reduction, and in the animals being cured. Thus, 15-deoxyspergualine is able to exert a therapeutic effect on the disease even after it has become manifest, not only in the sense of prolonging the survival time but also in the sense of effecting a cure. Cured animals showed no recurrence of their disease.

It is shown hereinafter that the concentrations of 15-deoxyspergualine which had a therapeutic effect on EAE had no immunosuppressive effect and resulted in no increase in the susceptibility to infection. For this purpose, rats were pretreated with 2.5 mg/kg 15-deoxyspergualine (orally or intraperitoneally) and were then infected with Listeria monocytogenes or Klebsiella pneumoniae. Table 3 shows that none of the animals treated with 2.5 mg of 15-deoxyspergualine died.

Increasing the dose of 15-deoxyspergualine to a range which is known to be immunosuppressive (5 mg/kg) Likewise increases the susceptibility to infection.

We claim:

1. A therapeutic method for the treatment of a mammal suffering from a non-cancer degenerative disease, which comprises administering to said mammal an effective amount of a pharmaceutical composition containing 15-deoxyspergualine.

2. A therapeutic method for the treatment of a mammal suffering from a non-cancer degenerative bone-marrow disease, which comprises administering to said mammal an effective amount of a pharmaceutical composition containing 15-deoxyspergualine.

3. A therapeutic method for the treatment of a mammal suffering from a non-cancer degenerative disease of the supporting and connective tissues, which comprises administering said mammal an effective amount of a pharmaceutical composition containing 15-deoxyspergualine.

4. A therapeutic method for the treatment of a mammal suffering from a non-cancer degenerative disease of the central nervous system, which comprises administering to said mammal an effective amount of a pharmaceutical composition containing 15-deoxyspergualine.

5. A therapeutic method for the treatment of a mammal suffering from a non-cancer degenerative kidney disease, which comprises administering to said mammal an effective amount of a pharmaceutical composition containing 15-deoxyspergualine.

6. A therapeutic method of treatment as claimed in claim 4, wherein the non-cancer degenerative disease of the central nervous system is multiple sclerosis.

7. A therapeutic method for the treatment of a mammal suffering from a non-cancer degenerative liver disease, which comprises administering to said mammal an effective amount of a pharmaceutical composition containing 15-deoxyspergualine.

8. The therapeutic method of treatment as claimed in claim 1, 2, 3, 4, 5, 6, or 7 wherein said 15-deoxyspergualine is in the form of the minus stereoisomer.

* * * * *